(12) United States Patent
Juaire (10) Patent No.: US 9,517,365 B2
(45) Date of Patent: Dec. 13, 2016

(54) PORTABLE OXYGEN SYSTEM

(71) Applicant: Stephen Juaire, Bonita Springs, FL (US)

(72) Inventor: Stephen Juaire, Bonita Springs, FL (US)

(*) Notice: Subject to any disclaimer, the term of this patent is extended or adjusted under 35 U.S.C. 154(b) by 328 days.

(21) Appl. No.: 14/205,516

(22) Filed: Mar. 12, 2014

(65) Prior Publication Data

US 2014/0261423 A1  Sep. 18, 2014

Related U.S. Application Data (60) Provisional application No. 61/788,755, filed on Mar. 15, 2013.

(51) Int. Cl.
| | | |
|---|---|---|
| *A62B 7/06* | (2006.01) | |
| *A61M 16/10* | (2006.01) | |
| *A62B 7/02* | (2006.01) | |
| *A61M 16/08* | (2006.01) | |
| *A62B 7/00* | (2006.01) | |
| *A61M 16/20* | (2006.01) | |
| *A62B 25/00* | (2006.01) | |

(52) U.S. Cl.
CPC ............ *A62B 7/06* (2013.01); *A61M 16/0816* (2013.01); *A61M 16/1005* (2014.02); *A61M 16/201* (2014.02); *A62B 7/00* (2013.01); *A62B 7/02* (2013.01); *A61M 2202/0208* (2013.01); *A61M 2202/03* (2013.01); *A61M 2205/8225* (2013.01); *A61M 2209/088* (2013.01); *A62B 25/00* (2013.01)

(58) Field of Classification Search
CPC ...... A61M 16/00; A61M 16/10; A61M 16/14; A62B 7/00; A62B 7/02; A62B 7/04; A62B 7/06; A62B 9/00; A62B 9/04; A62B 25/00; B63C 11/22; F17C 2270/025; F17C 2270/02; F17C 1/00; F17C 1/005; F17C 2201/00; F17C 2201/01; F17C 2201/0128; F17C 2201/0133; F17C 2201/0147; F17C 2201/054; F17C 2201/056
USPC ............ 128/200.24, 201.21, 204.18, 204.21, 128/205.13, 205.15, 205.22
See application file for complete search history.

(56) References Cited

U.S. PATENT DOCUMENTS

| | | | |
|---|---|---|---|
| 5,529,061 A | 6/1996 | Sanders | |
| 5,582,164 A * | 12/1996 | Sanders | ................... A62B 7/02 128/202.19 |
| 5,979,440 A * | 11/1999 | Honkonen | ........... B01D 5/0039 128/200.24 |
| 6,357,439 B1 | 3/2002 | Cook et al. | |
| 6,513,522 B1 | 2/2003 | Izuchukwu et al. | |

(Continued)

*Primary Examiner* — Justine Yu
*Assistant Examiner* — Colin W Stuart
(74) *Attorney, Agent, or Firm* — Vorys, Sater, Seymour and Pease LLP; Rex W. Miller, II (57) ABSTRACT

A container for storing oxygen under pressure is disclosed that includes a chamber adapted to be worn around a user's waist and adapted for supplying oxygen to the user; the chamber defining a volume to contain oxygen under pressure; wherein the chamber is defined by a central portion extending between opposite side portions; wherein each of the opposite side portions has a height greater than a maximum height of the central portion that further defines a void between the side portions and above the central portion; and wherein the chamber is further defined by an exterior surface of the chamber adjacent the user.

15 Claims, 11 Drawing Sheets

(56) References Cited

U.S. PATENT DOCUMENTS

| | | | |
|---|---|---|---|
| 6,513,523 B1 | 2/2003 | Izuchukwu et al. | |
| 6,526,968 B1 | 3/2003 | Izuchukwu et al. | |
| 6,651,659 B2 | 11/2003 | Izuchukwu | |
| 7,156,092 B2 | 1/2007 | Otter | |
| 7,624,761 B2 | 12/2009 | Arnold et al. | |
| 2003/0005933 A1* | 1/2003 | Izuchukwu | A61M 16/0677 128/205.22 |
| 2005/0103342 A1* | 5/2005 | Jorczak | A61M 16/00 128/205.24 |
| 2007/0039616 A1* | 2/2007 | Hughes | F17C 6/00 128/201.21 |

* cited by examiner

PORTABLE OXYGEN SYSTEM

CROSS-REFERENCE TO RELATED APPLICATION

This application claims priority to and the benefit of U.S. Provisional Application No. 61/788,755, filed on Mar. 15, 2013, the disclosure of which is incorporated herein by reference.

BACKGROUND AND SUMMARY

Supplement oxygen is often prescribed for patients with respiratory problems or other medical conditions. Many of the medical conditions that necessitate the use of supplemental oxygen are chronic conditions causing the patient to become a user of supplement oxygen for an extended period of time, and often for the remainder of the patient's life.

For home use, stationary base systems are often provided that are capable of supplying large amounts of oxygen over extended periods of time. These base systems may operate to condense oxygen from the atmosphere or may be refilled periodically with deliveries of liquid oxygen. While the home systems are capable of providing large quantities of oxygen over extended periods of time, these home systems are not portable and the user's range of motion is typically limited to the length of the lumen used to delivery oxygen from the base system to the user.

When a supplement oxygen user desires to venture away from their base system, the user may utilize a portable oxygen delivery system. Some portable oxygen delivery systems have been configured to be worn, such as in a backpack, fanny back or other configuration in order to allow the user greater mobility and freedom of movement. Examples of wearable portable oxygen delivery systems may be found in U.S. Pat. Nos. 6,651,659 and 6,513,523. A consistent drawback of existing wearable portable oxygen systems has been the limited oxygen storage capacity and the corresponding limited duration for which these systems may be used, particularly when a user's medical condition warrants a constant flow of gaseous oxygen. Faced with the possibility of their portable oxygen supply running out, many users reduce the flow rate of their supplemental oxygen or switch from a constant flow to a pulsed flow in order to conserve the limited supply of oxygen in their portable system. By reducing the rate of consumption, the user is able to extend the duration of use of the portable system but must sacrifice some of the medical benefit.

For users who require a constant flow of oxygen or a longer duration of use, supplemental oxygen users have been forced to forego the wearable portable systems and rely upon a high capacity portable oxygen systems. High capacity portable systems often include a larger tank for storing the required volume of oxygen. Due to the size and weight, many high capacity portable systems are configured such that the tank may be pulled on a cart. Alternatively, those users with sufficient strength may carry the tank. Although these high capacity systems are portable in that the tank may be moved between locations, the need to pull or carry the tank imposes a significant burden on the supplement oxygen user. The restricted movement and cumbersome nature of the high capacity systems often prevents users of such systems from participating in physical activities that they are otherwise capable of performing. Even if the user is capable of carrying the high capacity oxygen system, the configuration of such systems often interfere with the user's range of motion and mobility by distorting the user's center of balance. Beneficial physical activities, such as golf, thus become very difficult for users of supplement oxygen.

In view of the limitations of existing designs, there remains a need for portable oxygen delivery systems that provide an ergonomic means for storing oxygen in a wearable configuration without substantially inhibiting the user's movement, and that provide high storage capacity to accommodate both an oxygen delivery rate and a duration of use that enable the supplement oxygen user to participate in their desired physical and recreational activities.

Provided is a container for storing oxygen under pressure. In one embodiment, the chamber is configured to be worn around a user's waist for supplying oxygen to the user, the chamber defining a volume sized to contain at least one liquid liter of oxygen under pressure, wherein the chamber is defined by a central portion extending between opposite side portions, and the side portions are configured to wrap at least partially around the user's waist such that an exterior surface of the chamber adjacent the user is substantially concave, and wherein each of the opposite side portions has a height greater than a maximum height of the central portion that further defines a void between the side portions and above the central portion. In another embodiment, the void is sized to receive an oxygen delivery system. In another embodiment, the volume is sized to contain at least 750 liters gaseous equivalent capacity. In another embodiment, the chamber has a rigid exterior. In another embodiment, each of the opposite side portions has an interior side portion volume, and the central portion has an interior central portion volume, and the interior side portion volume is equal to or greater than the interior central portion volume. In another embodiment, the volume of the chamber is continuous without dividers or partitions within the volume. In another embodiment, the chamber has a lateral cross-section that is generally kidney shaped to conform to a user's torso. In some embodiments, the chamber defining a volume is sized to contain at least 1.5 liquid liters of oxygen under pressure. In some embodiments, the chamber defining a volume is sized to contain at least 0.75 liquid liters of oxygen under pressure.

Also disclosed is a portable oxygen delivery system that includes a chamber configured to be worn around a user's waist, the chamber defining a volume sized to contain at least one liquid liter of oxygen under pressure, wherein the chamber is defined by a central portion extending between opposite side portions, and the side portions are configured to wrap at least partially around the user's waist to form a first curvature of the chamber, and wherein each of the opposite side portions has a height greater than a maximum height of the central portion that further defines a void between the side portions and above the central portion, an oxygen delivery system disposed in the void between the opposite side portions of the chamber, the oxygen delivery system including: an oxygen supply line coil connected to an output port of the chamber, a flow control valve configured to regulate the flow of gaseous oxygen to the user, and a lumen connector configured to receive a lumen for delivering the flow of gaseous oxygen to the user. In another embodiment, the system is configured to provide a constant flow demand of at least 2 gaseous liters per minute for duration of at least 6 hours. In another embodiment, the volume is sized to contain at least 750 liters gaseous equivalent capacity. In another embodiment, the system includes a carrying case containing the chamber and oxygen delivery system, the carrying case configured to be secured around a user's waist. In another embodiment, the flow control valve is an electronically controlled flow control valve, and wherein the portable oxygen system further comprises a remote control configured to communicate wirelessly with the electronically controlled flow control valve to adjust the flow of gaseous oxygen to the user.

Also disclosed is a portable oxygen delivery system that includes means for ergonomically storing at least 750 liters gaseous equivalent capacity of oxygen under pressure in a configuration that is wearable by a user about the user's waist without substantially inhibiting the user's movement, and an oxygen delivery system for delivering gaseous oxygen to the user.

BRIEF DESCRIPTION OF THE DRAWINGS

Reference is made to the accompanying drawings in which particular embodiments of the invention are illustrated as described in more detail in the description below, in which.

DETAILED DESCRIPTION OF THE DRAWINGS

Referring generally to FIGS. 1-18, shown are embodiments of a portable oxygen delivery system that provides an ergonomic means for storing oxygen under pressure in a configuration that is wearable by a user about the user's waist without substantially inhibiting the user's movement. The presently disclosed system and components enable oxygen users, and particularly continuous flow oxygen users, increased mobility and significant lifestyle improvements over the conventional systems presently available. These improvements may further improve oxygen users' adherence to recommended oxygen delivery rates by facilitating the use of portable oxygen without the adverse lifestyle consequences of prior systems.

Figure 1:
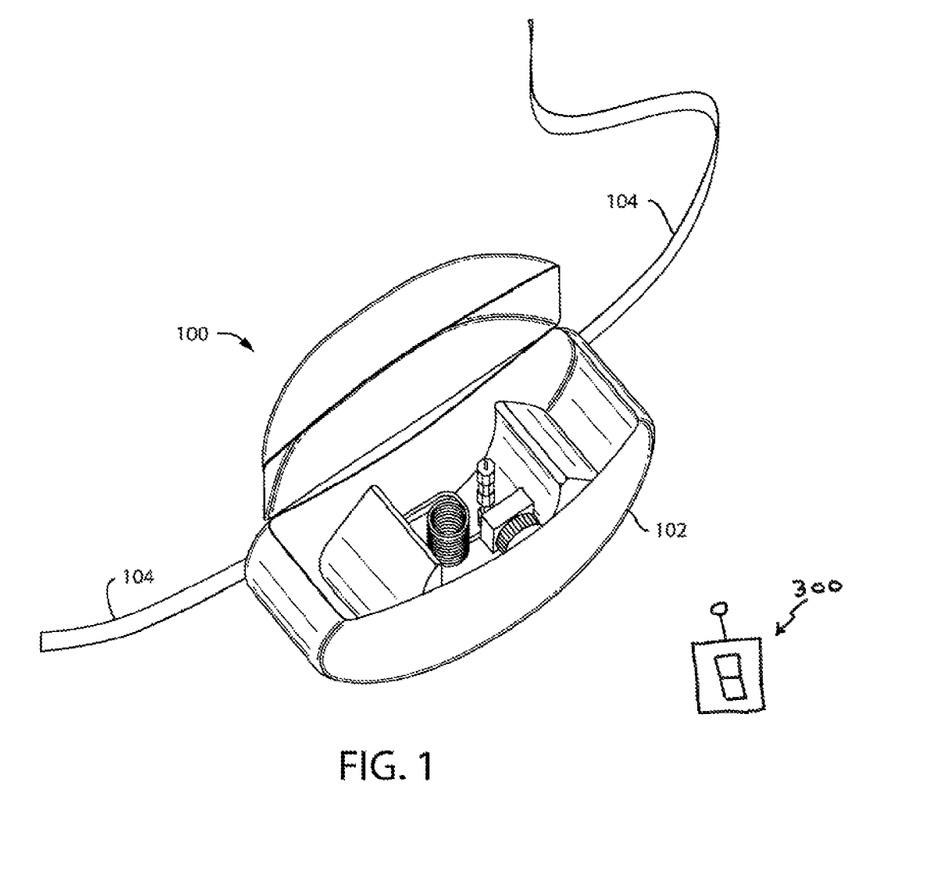
FIG. 1 is a perspective view of a portable oxygen system in a carrying case.

Referring now to FIG. 1, an embodiment of a portable oxygen system 100 is illustrated. The portable oxygen system 100 includes a case 102 configured to house a chamber 120 and oxygen delivery components. A lumen (not shown) extends from the oxygen delivery components and out of the case to supply the user with oxygen. The case 102 is configured to be worn about the user's waist, and may be secured to the user with the belt 104. In this manner, the portable oxygen system 100 is configured to be worn by a user without substantially inhibiting the user's freedom of movement or range of motion.

Figure 2:
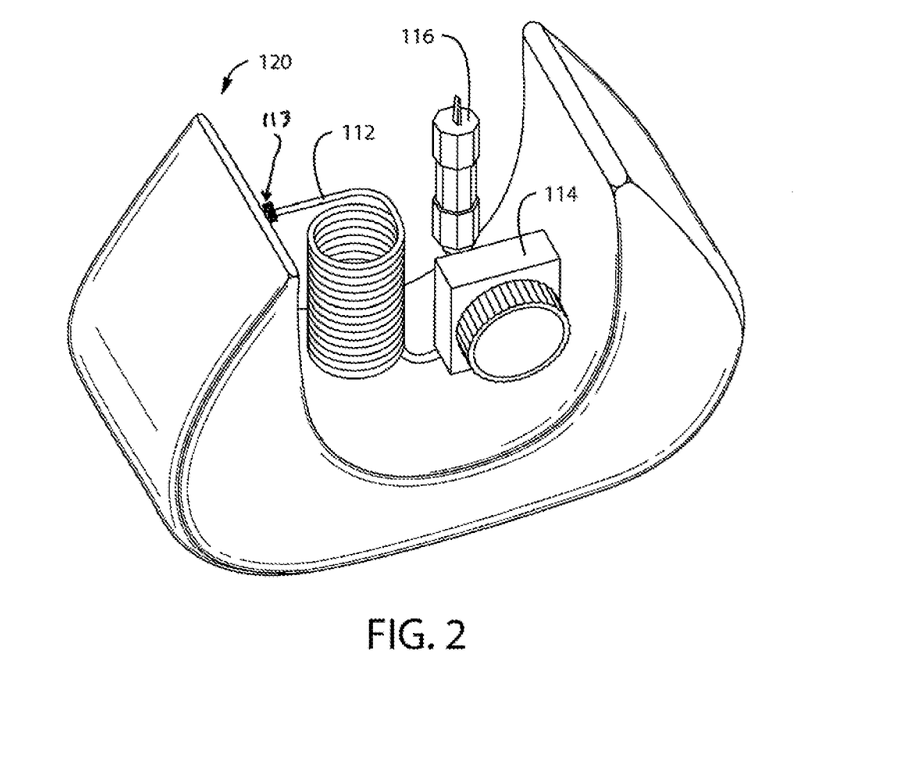
FIG. 2 is a perspective view of a portable oxygen system not in a carrying case.

Referring now to FIG. 2, the chamber 120 and oxygen delivery components are further illustrated removed from the case. The chamber 120 defines a volume for storing oxygen under pressure. In some embodiments, the volume of the chamber 120 may be sized to contain 0.75 liquid liters of oxygen under pressure, 1.0 liquid liters of oxygen under pressure, or 1.5 liquid liters of oxygen under pressure. In certain embodiments it may be possible to get acceptable functionality from a chamber 120 having a volume as low as 0.5 L. The oxygen contained may be in a liquid or gaseous state or a mixture of liquid and gas depending upon the temperature and operating conditions. In any event, the chamber 120 is sized to provide a constant flow demand of at least two (2) gaseous liters per minute for a duration of at least five (5) hours. In embodiments, the volume of the chamber is sized to provide at least 750 liters gaseous equivalent capacity. The capability of providing constant flow demand over an extended time period, such as five (5) hours, has typically required the use of oxygen system employing a cylindrical tank that must be pulled on cart or carried by the user substantially interfering with the user's mobility and range of motion. The chamber 120 presently disclosed however is configured to be worn without inhibiting movement while also providing a sufficient supply of oxygen to satisfy a constant flow demand avoiding the common tradeoff between adequate oxygen supply and lifestyle impact made by many users who require portable oxygen. The chamber 120 is configured to provide the needed volume as a larger area extending across, or along an area substantially coincident with, the user's back and extending slightly from the user's back so as to reduce or minimize the distance of the center of gravity from the user's back. This reduction or minimization of the distance of the center of gravity from the user's back is helpful in minimizing or reducing the impact on a user's balance and mobility and thereby preventing inhibition of movement or other lifestyle impact.

Figure 3:
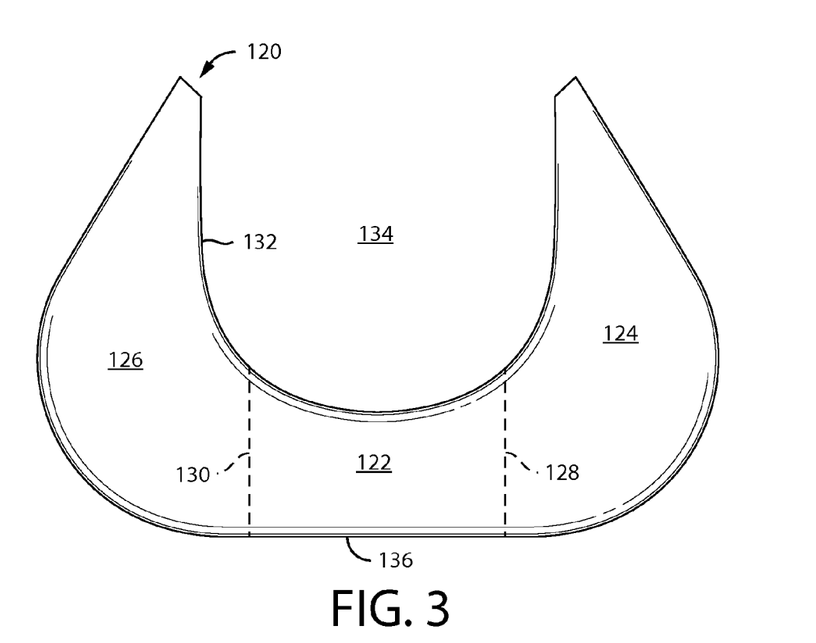
FIG. 3 is a front view of a container for storing oxygen for use in a portable oxygen system.

As illustrated in FIGS. 2-3, the oxygen delivery components may be provided in a void 134 defined between opposite side portions 124, 126 of the chamber 120. In some embodiments, the oxygen delivery components may include an oxygen supply line coil 112 connected to an output port 113 of the chamber 120. The oxygen supply line coil 112 communicates oxygen from the chamber to a flow control valve 114 that regulates the flow of oxygen to the user. The oxygen may then flow to a lumen connector 116 to which a lumen may be attached to deliver the oxygen to the user. To improve the ergonomics of the portable oxygen delivery system, the oxygen delivery components are positioned near the center of mass of the chamber 120 so as to minimize the impact on a user's balance and mobility.

Figure 4:
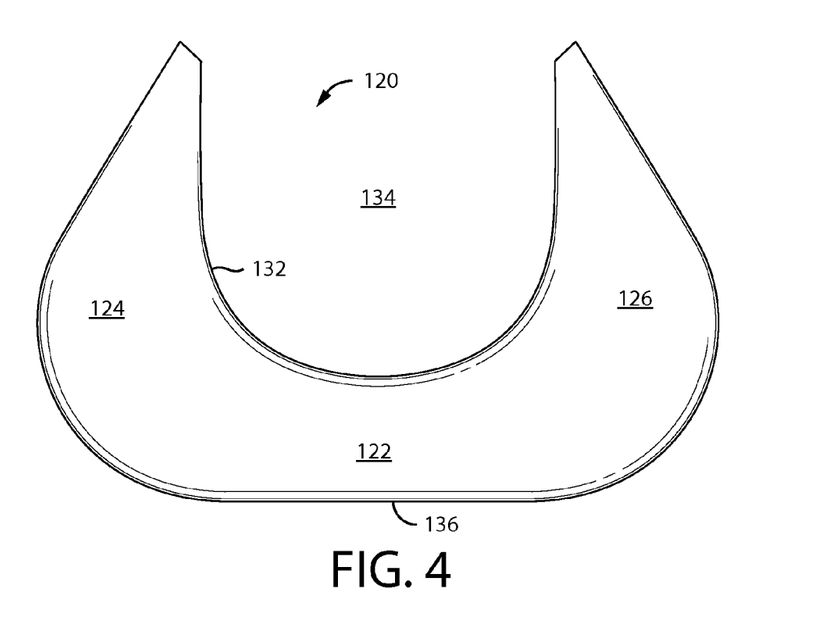
FIG. 4 is a back view of the container of FIG. 3.

Referring now to FIGS. 3-9, the chamber 120 of the portable oxygen delivery system is further described. FIGS. 3 and 4 illustrate front and back views of the chamber 120. To accommodate the increased volume relative to prior oxygen systems, in this non-limiting embodiment, the chamber 120 is generally U-shaped with a central portion 122 and opposite side portions 124, 126, all in fluid communication with each other. The U-shaped construction allows the chamber to utilize both horizontal and vertical dimensions to increase capacity while maintaining an ergonomic configuration that is wearable by a user. In some embodiments, the depth of the chamber 120, that is, how far it extends outward from the body of the user, correlates to imbalance and interference with ergonomics, such that it may be desirable to reduce or minimize extension in the depth dimension. In some embodiments, in which it may be desirable to reduce or minimize extension in the depth dimension, the desired volume may be attained by increasing the extension of the chamber 120 in one or more of the horizontal and vertical dimensions, those dimensions perpendicular to the depth dimension. In some embodiments, the horizontal and vertical dimensions substantially correspond to an area substantially coincident with the users back.

In one embodiment, the chamber 120 has a continuous hollow interior without partitions or dividers between the respective portions thereby maximizing the available capacity for storing oxygen. In many embodiments the chamber 120 has a continuous exterior that is continuous across the boundaries 128, 130 between the central portion 122 and the side portions 124, 128. The chamber 120 may further have a substantially planar bottom 136. The bottom 136 of the chamber may be planar only in the region beneath the central portion 122 with the bottom of the chamber curving upwards in transition to the side portions. The contour of the bottom portion may be configured to facilitate a user bending and twisting about the waist, such as may occur during physical activities such as golf.

As shown in FIGS. 3 and 4, each of the side portions 124, 126 has a height (as measured in the vertical direction as the chamber is configured to be worn by a user). The maximum height of the side portions is greater than the maximum height of the central portion. This difference in height defines the generally U-shaped construction of the chamber 120, and also defines a void 134 between the side portions and above the central portion, such as illustrated in FIG. 3. The configuration of the chamber 120 creates a void 134 sized to receive components of an oxygen delivery system, such as the coil 112, flow regulator 114, and lumen connector 116 previously discussed. In some embodiments, the oxygen delivery components may be secured to the surface 132 in such a manner to maintain the center of mass of the system near the geometric center thereby allowing the portable oxygen system to be worn without substantially disrupting a user's balance. In some embodiments, the oxygen delivery components may be secured within the region defined by void 134 such that the oxygen delivery components are substantially shrouded by the chamber 120.

In order to further distribute the weight of the portable oxygen system in an ergonomically desirable manner, the interior volume of the side portions 124, 126 may be equal to or greater than the interior volume of the central portion 122. When the chamber 120 is filled with oxygen under pressure, the mass of the stored oxygen adds to the weight of the portable oxygen delivery system. Prior systems have tended to utilize a single tank or container or a collection of small, interconnected containers in a close configuration. In contrast, the presently disclosed chamber distributes the oxygen between the central portion 122 and the side portions 124, 126 so that the weight of the stored oxygen is distributed around a greater portion of the user's waist. The interior volume of the side portions 124, 126 may be increased relative to the central portion 122 so that the weight of the oxygen is offset from the weight of the oxygen delivery components positioned above the center portion 122. In this manner, the volume of the chamber 120 of the portable oxygen delivery system may be increased to supply at least 750 liters gaseous equivalent capacity, while maintaining the wearable configuration that does not substantially inhibit a user's movement.

Figure 5:
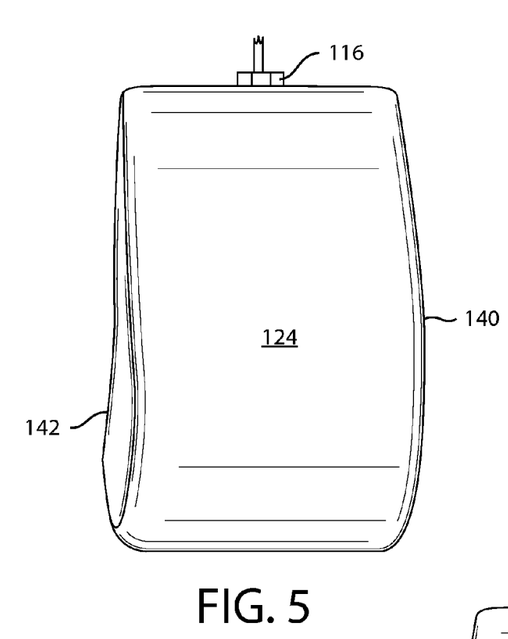
FIG. 5 is a right side view of the container of FIG. 3.
Figure 6:
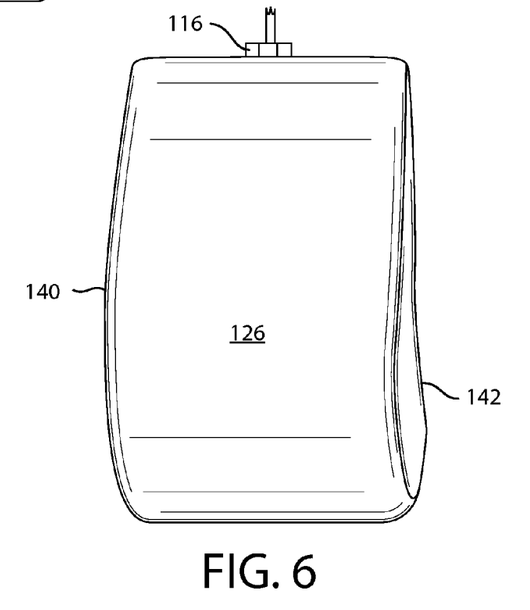
FIG. 6 is a left side view of the container of FIG. 3.

The chamber 120 may be further configured to distribute the weight of the oxygen about a user's waist. Referring to FIGS. 5 and 6, right and left side views of the chamber 120 are illustrated. As shown, the chamber 120 has a user facing side 140 and an outward facing side 142. For clarity, the user facing side 140 is the side of the chamber that faces the user's torso when the user wears the portable oxygen system illustrated in FIG. 1. The outward facing side 142 is opposite the user facing side 140 and generally faces away from the user's torso.

Figure 7:
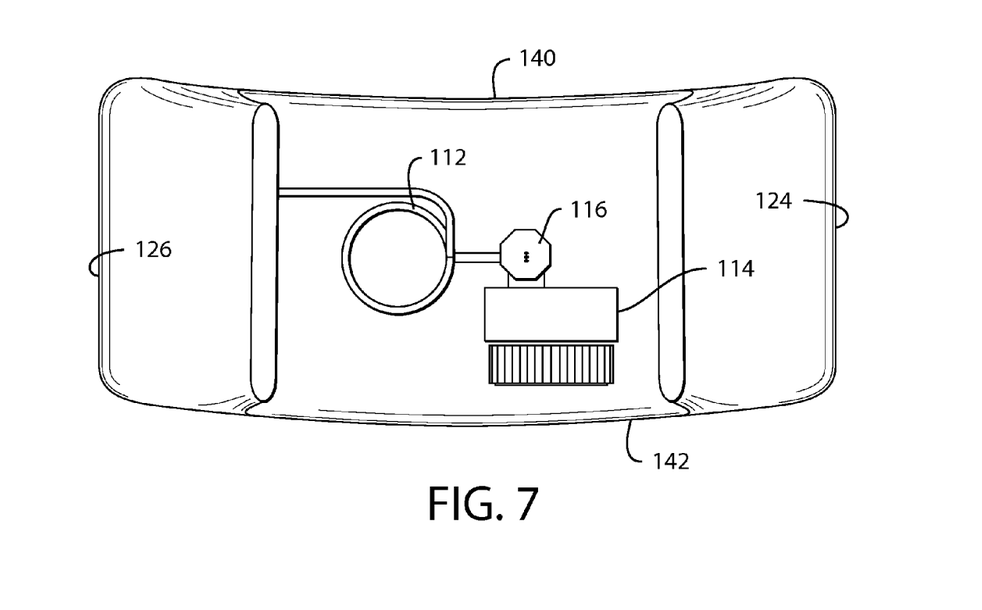
FIG. 7 is a top view of the container of FIG. 3.
Figure 8:
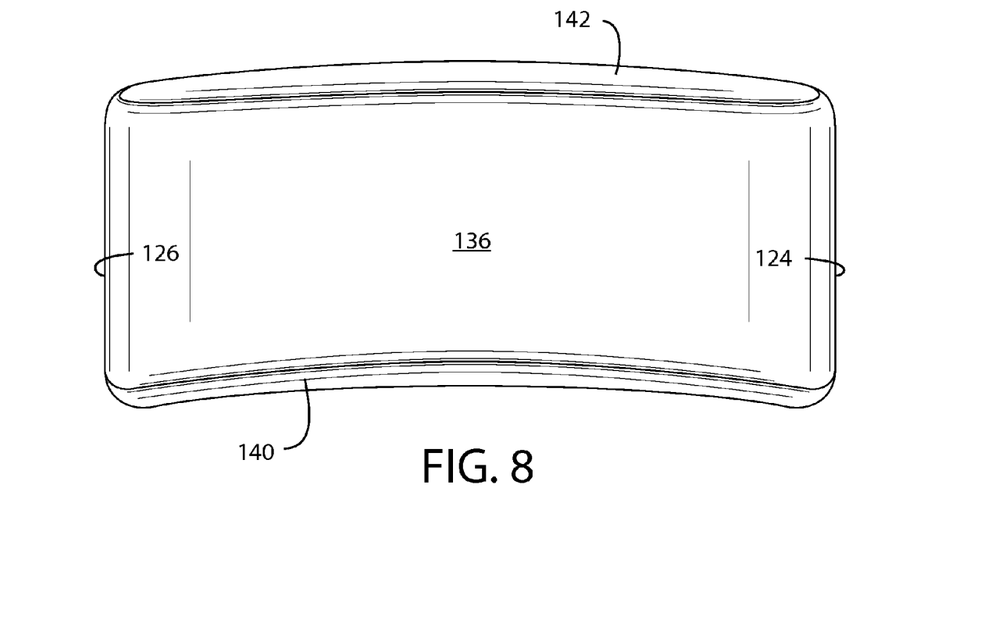
FIG. 8 is a bottom view of the container of FIG. 3.
Figure 9:
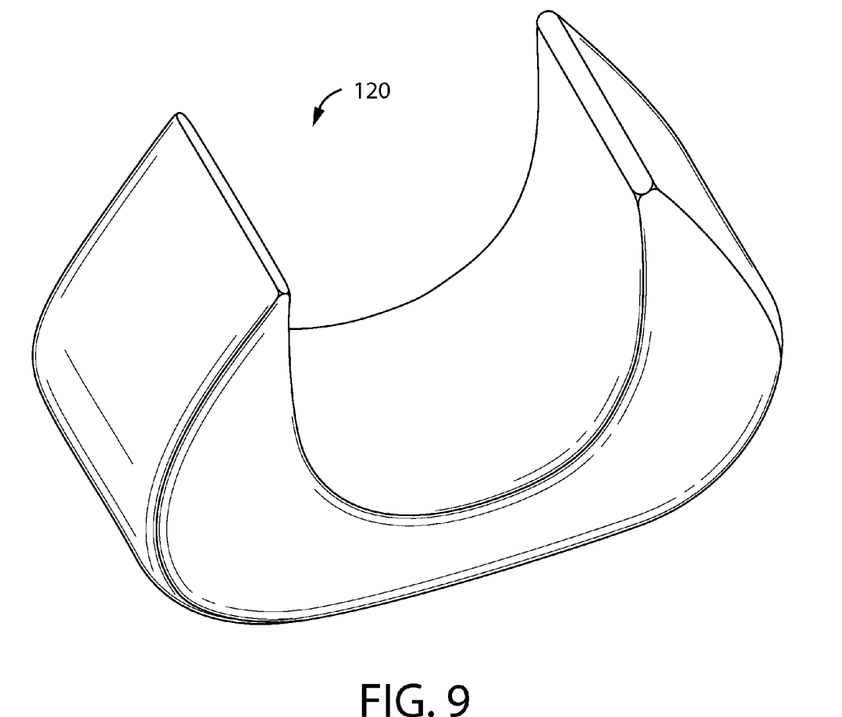
FIG. 9 is a perspective view of the container of FIG. 3.

Referring now to FIGS. 7 and 8, top and bottom views of the chamber 120 are illustrated. As illustrated, in some embodiments, the user facing side 140 is substantially concave such that the user facing side 140 accommodates the general curvature of a user's torso when worn in the carrying case such as illustrated in FIG. 1. In embodiments in which the user facing side 140 is substantially concave, in order to maintain the desired weight distribution, the outward facing side 142 of the chamber 120 may be substantially convex. Accordingly, in some embodiments, the chamber 120 may therefore be described as having a lateral cross-section that is generally kidney shaped to accommodate a user's torso, where the lateral cross-section is a cross-section taken parallel to a user's waist. A perspective view of the chamber 120 is illustrated in FIG. 9 which further illustrates the configuration of the chamber previously described.

A second embodiment of the portable oxygen system 100' is shown in FIGS. 11-18. The portable oxygen system 100' includes a case 102' configured to house a chamber 120' and oxygen delivery components 110'. A lumen 116' extends from the oxygen delivery components 110' and out of the case 102' to supply the user with oxygen. The case 102' is configured to be worn about or proximate to the user's waist, and may be secured to the user with a belt or similar device. As illustrated, in some embodiments the case 102' may comprise a user facing surface side 140' that is substantially concave, such that the user facing surface side 140' accommodates the general curvature of a user's torso when worn. The portable oxygen system 100' is configured to be worn by a user without substantially inhibiting the user's freedom of movement or range of motion.

With continued reference to FIGS. 11-18, the chamber 120' and oxygen delivery components 110' are further illustrated in various orientations and section views. The chamber 120' defines a volume for storing oxygen under pressure. In some embodiments, the volume may be sized to contain 0.75 liquid liters of oxygen under pressure, 1.0 liquid liters of oxygen under pressure, or 1.5 liquid liters of oxygen under pressure. The oxygen contained may be in a liquid or gaseous state or a mixture of liquid and gas depending upon the temperature and operating conditions. In any event, the chamber 120' may be sized to provide a constant flow demand of at least two (2) gaseous liters per minute for a duration of at least five (5) hours. In some embodiments, the volume of the chamber is sized to provide at least 750 liters gaseous equivalent capacity. The chamber 120' presently disclosed is configured to be worn, without limitation, in a case 102', without substantially inhibiting movement while also providing a sufficient supply of oxygen to satisfy a constant flow demand avoiding the common tradeoff between adequate oxygen supply and lifestyle impact made by many users who require portable oxygen.

With continued reference to FIGS. 11-18, the oxygen delivery components 110' may be provided in a void 134' defined between opposite side portions 124', 126' of the chamber 120'. In some embodiments, the oxygen delivery components 110' may include an oxygen supply line coil 112' connected to an output port (not shown) of the chamber. The oxygen supply line coil 112' communicates oxygen from the chamber 120' to a flow control valve 114' that regulates the flow of oxygen to the user. The oxygen may then flow to a lumen connector 116' to which a lumen may be attached to deliver the oxygen to the user. To improve the ergonomics of the portable oxygen delivery system, the oxygen delivery components 110' are positioned near the center of mass of the chamber 120' so as to reduce or minimize the impact on a user's balance and mobility.

Figure 11:
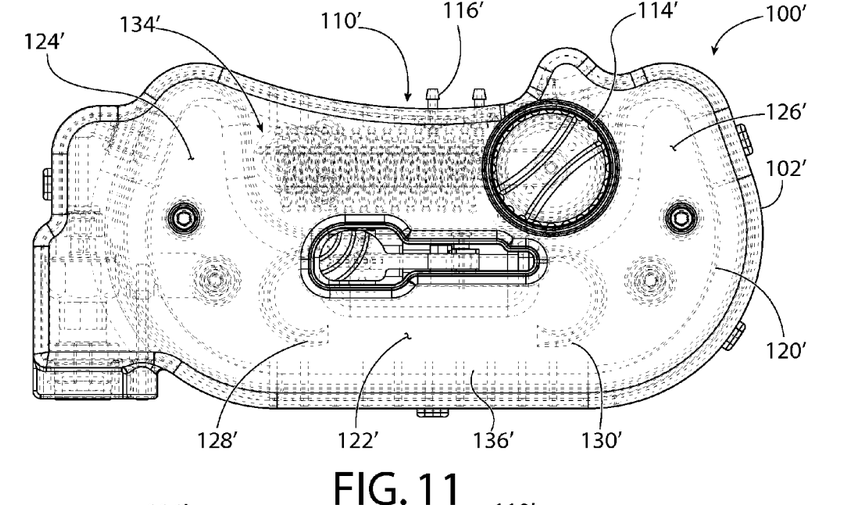
FIG. 11 is a front view of a second embodiment of a portable oxygen system.
Figure 12:
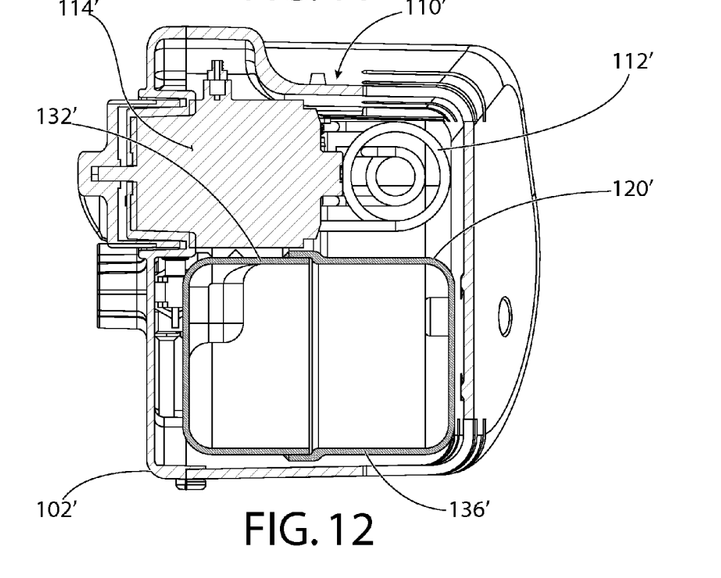
FIG. 12 is a section view of the second embodiment of a portable oxygen system.
Figure 13:
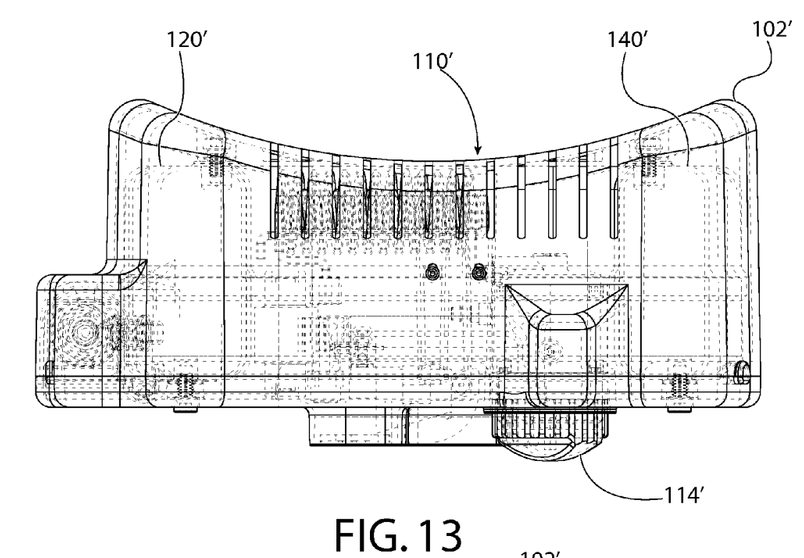
FIG. 13 is a top view of the second embodiment of a portable oxygen system.
Figure 14:
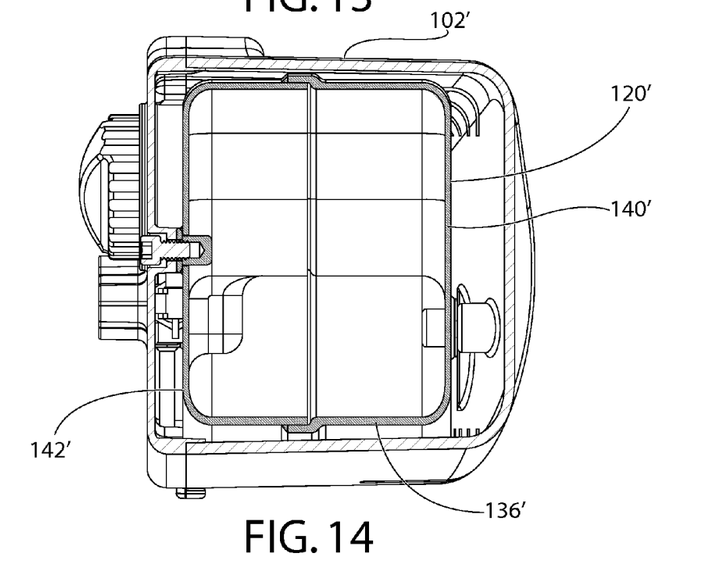
FIG. 14 is a section view of the second embodiment of a portable oxygen system.
Figure 15:
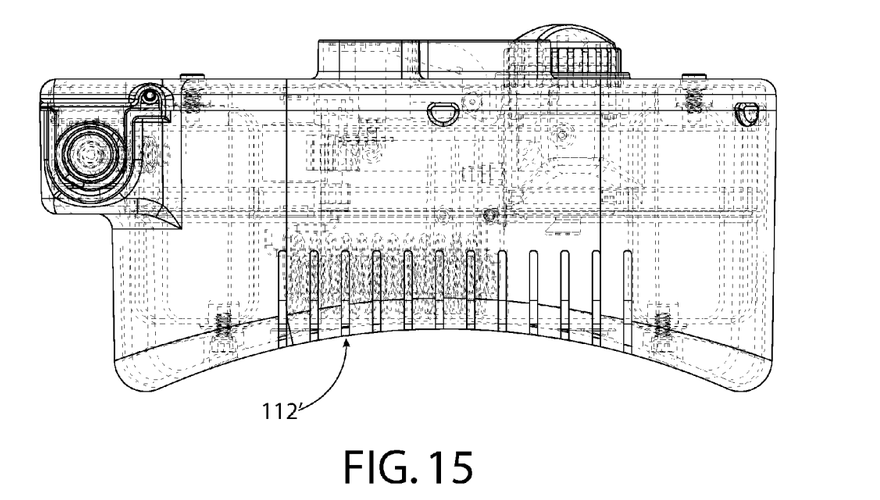
FIG. 15 is a bottom view of the second embodiment of a portable oxygen system.
Figure 16:
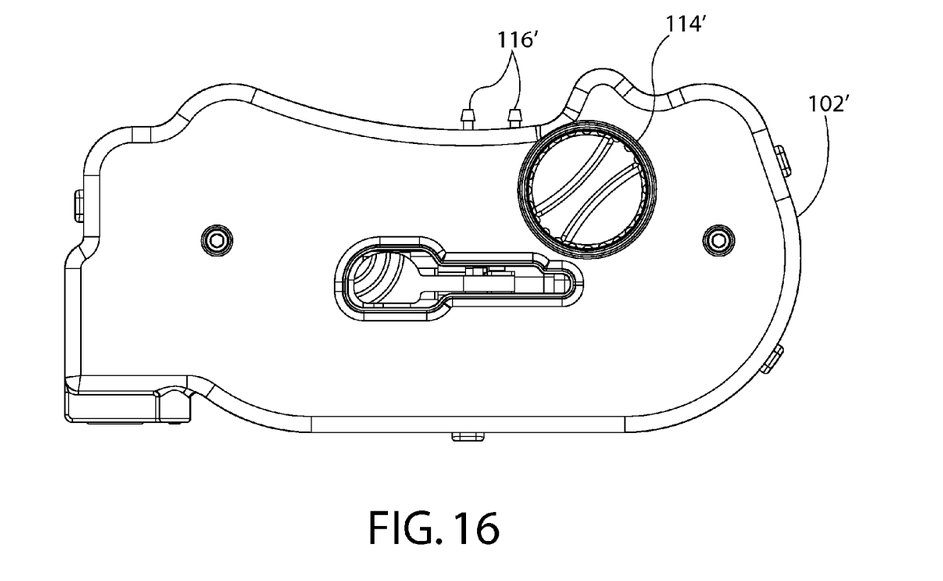
FIG. 16 is another front view of the second embodiment of a portable oxygen system.

With continued reference to FIGS. 11-18, the chamber 120' of the portable oxygen system 100' is further described. FIG. 11 shows the back of the chamber 120'. To accommodate the increased volume relative to prior oxygen systems, in this non-limiting embodiment, the chamber 120' is generally U-shaped with a central portion 122' and opposite side portions 124', 126', all in fluid communication with each other. The U-shaped construction allows the chamber 120' to utilize both horizontal and vertical dimensions to increase capacity while maintaining an ergonomic configuration that is wearable by a user. In some embodiments, the depth of the chamber 120', that is, how far it extends outward from the body of the user, correlates to imbalance and interference with ergonomics, such that it may be desirable to reduce or minimize extension in the depth dimension. In some embodiments, in which it may be desirable to reduce or minimize extension in the depth dimension, the desired volume may be attained by increasing the extension of the chamber 120' in one or more of the horizontal and vertical dimensions, those dimensions perpendicular to the depth dimension. As noted above, in certain embodiments, the horizontal and vertical dimensions may substantially correspond to an area substantially coincident with the users back. In one embodiment, the chamber 120' has a continuous hollow interior without partitions or dividers between the respective portions thereby maximizing the available capacity for storing oxygen. In many embodiments the chamber 120' has a continuous exterior that is continuous across the boundaries 128', 130' between the central portion 122' and the side portions 124', 128'. The chamber 120' may further have a substantially planar bottom 136'. The bottom 136' of the chamber may be planar only in the region beneath the central portion 122' with the bottom of the chamber curving upwards in transition to the side portions. The contour of the bottom portion may be configured to facilitate a user bending and twisting about the waist, such as may occur during physical activities such as golf.

With continued reference to FIGS. 11-18, each of the side portions 124', 126' has a height (as measured in the vertical direction as the chamber is configured to be worn by a user). The maximum height of the side portions is greater than the maximum height of the central portion 122'. This difference in height defines the generally U-shaped construction of the chamber 120', and also defines a void 134' between the side portions 124', 126' and above the central portion 122', such as illustrated in FIG. 11. The configuration of the chamber 120' creates a void 134' sized to receive components of an oxygen delivery system 100', such as the coil 112', flow control valve 114', and lumen connector 116' previously discussed. In some embodiments, the oxygen delivery components 110' may be secured to the surface 132' in such a manner to maintain the center of mass of the system near the geometric center thereby allowing the portable oxygen system 100' to be worn without substantially disrupting a user's balance.

In order to further distribute the weight of the oxygen delivery system 100' in an ergonomically desirable manner, the interior volume of the side portions 124', 126' may be equal to or greater than the interior volume of the central portion 122'. When the chamber 120' is filled with oxygen under pressure, the mass of the stored oxygen adds to the weight of the portable oxygen delivery system 100'. The chamber 120' shown in FIGS. 11-18 distributes the oxygen between the central portion 122' and the side portions 124', 126' so that the weight of the stored oxygen is distributed around a greater portion of the user's waist. The interior volume of the side portions 124', 126' may be increased relative to the central portion so that the weight of the oxygen is offset from the weight of the oxygen delivery components 110' positioned above the center portion 122'. In this manner, the volume of the chamber 120' of the portable oxygen delivery system may be increased to supply at least 750 liters gaseous equivalent capacity, while maintaining the wearable configuration that does not substantially inhibit a user's movement.

The chamber 120' may be further configured to distribute the weight of the oxygen about a user's waist. Referring to FIGS. 11, 12, 14, and 18, multiple views of the chamber 120' are illustrated. As shown, the chamber 120' has a user facing side 140' and an outward facing side 142'. For clarity, the user facing side 140' is the side of the chamber that faces the user's torso when the user wears the portable oxygen system illustrated in FIGS. 11-18. The outward facing side 142' is opposite the user facing side and generally faces away from the user's torso.

Figure 17:
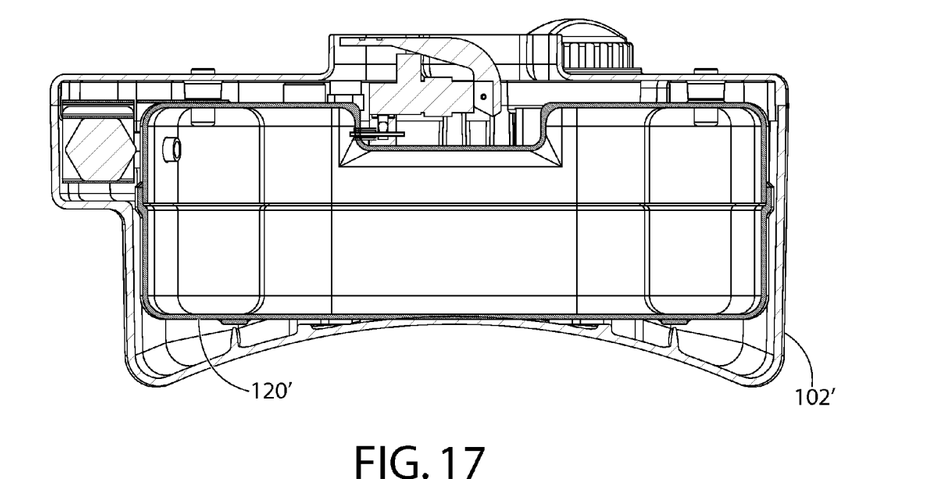
FIG. 17 is a section view of the second embodiment of a portable oxygen system.
Figure 18:
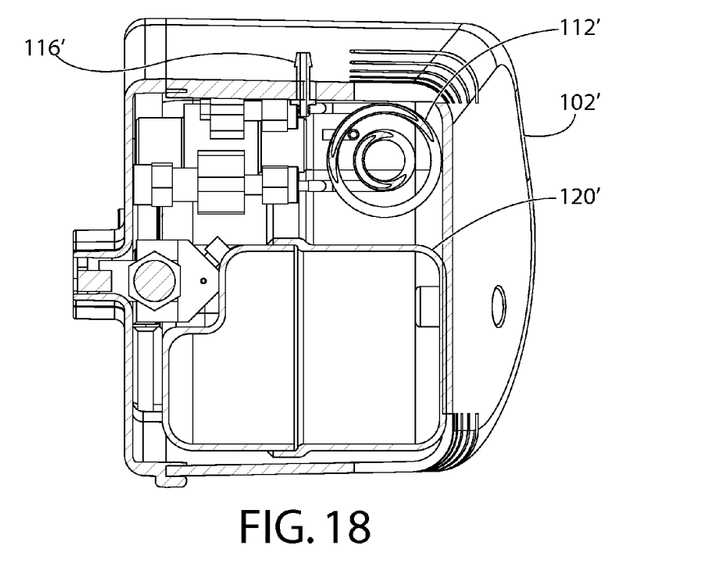
FIG. 18 is another section view of the second embodiment of a portable oxygen system.

With continued reference to FIGS. 11, 12, 14, and 18, in some embodiments, the user facing side 140' is substantially planar. In some embodiments in which the user facing side 140' is substantially planar, in order to maintain the desired weight distribution, the outward facing side 142' of the chamber 120' may be substantially planar. Accordingly, in some embodiments, the chamber 120' may therefore be described as having a lateral cross-section that is generally rectangular as shown in FIG. 17 where the lateral cross-section is a cross-section taken parallel to a user's waist.

The contrast between the embodiment shown in FIGS. 1-10, and the embodiment shown in FIGS. 11-18 shows that, the present subject matter covers multiple embodiments. Embodiments covered include, without limitation, those in which the lateral cross section of the chamber 120, 120' may be rectangular, kidney-shaped, or curved in some other way chosen with good engineering judgment. Embodiments covered include, without limitation, those in which the side portions 124, 126, 124', 126' may extend upwards from the central portion 122, 122' by a large distance, by a small distance, or by some distance with good engineering judgment. Embodiments covered include, without limitation, those in which the side portions 124, 126, 124', 126' terminate in a radius, an angle, or by some other form chosen with good engineering judgment.

Figure 10:
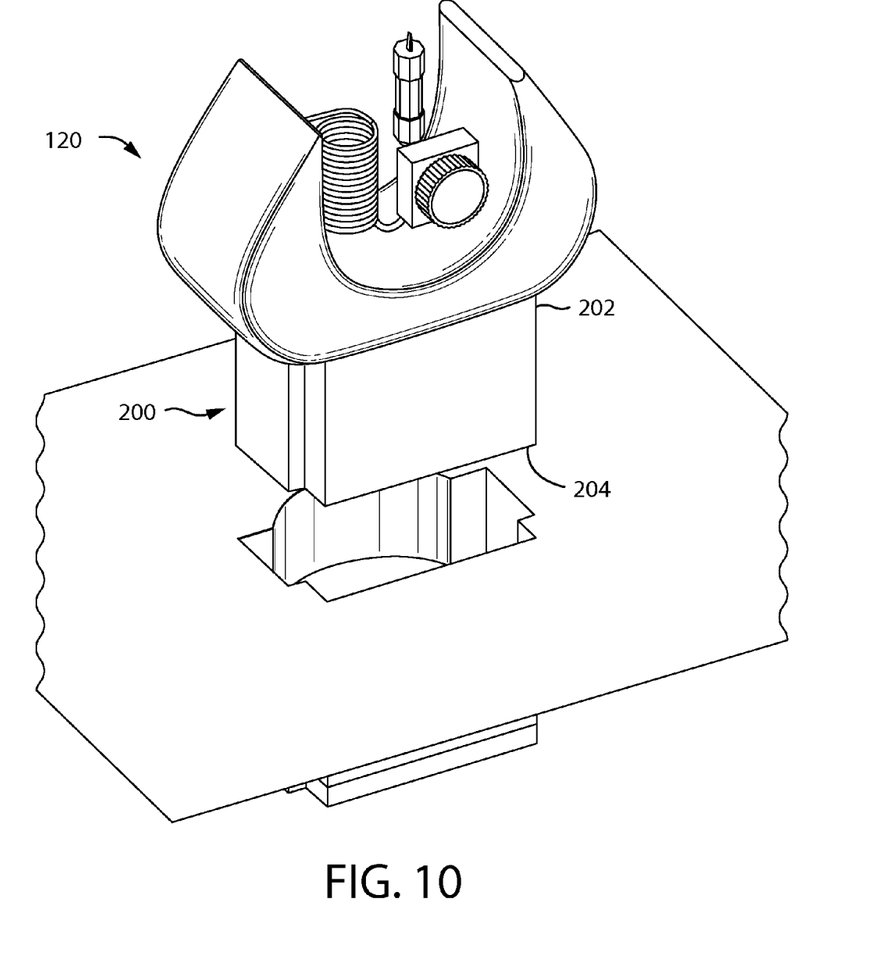
FIG. 10 is a perspective view of a refill adapter for use with a portable oxygen system.

Referring now to FIG. 10, a refill adapter for use with a portable oxygen delivery system is illustrated. Users of portable oxygen often maintain a stationary base system in their home that is used as a source of supplemental oxygen when the user in their home and/or to refill the user's portable oxygen delivery system. Currently, most portable oxygen delivery systems are specifically designed to mate with a corresponding base system. As a practical matter, once a user has selected a base system from a given manufacturer, the user is forced to select a portable oxygen delivery system from the same manufacturer so that the portable system may be refilled from the base system. Presently disclosed is a refill adapter 200 having a first interface 202 configured to engage the presently disclosed portable oxygen delivery system, and a second interface 204 configured to engage a base system. The first interface 202 includes a first connector that mates with an oxygen input port of the chamber 120. The oxygen input port may be positioned on the bottom 136 of the chamber 120, and the first interface may conform to the bottom of the chamber to facilitate mating of the first connector with the oxygen input port. The second interface 204 may be configured to mate with an oxygen output port of one or more base systems and the shape of the second interface may accommodate mating with one or more base systems. The first connector and second connector of the refill adapter are connected in fluid communication so that oxygen may be passed from the base system, through the refill adapter, and into the chamber 120 to fill the chamber with oxygen. In embodiments, the refill adapter may further include one or more interlocks to prevent the flow of oxygen from the base system unless the chamber 120 is securely mated to the first connector. In this manner, inadvertent leakage of oxygen may be avoided during the refill process. A refill adapter constructed in this manner enables the presently disclosed portable oxygen system to be used with a variety of existing base systems, and frees a user to select a portable oxygen delivery system from a manufacturer other than the manufacturer of their stationary base system.

In some embodiments, the portable oxygen delivery system includes an electronically controlled flow control valve. The portable oxygen delivery system may include a remote control 300 configured to communicate wirelessly with the electronically controlled flow control valve. The portable oxygen system is configured to be ergonomically worn by a user. It is contemplated that the system will often be worn in a pack worn around the user's waist with the chamber and oxygen delivery system positioned in the back, as in a fanny pack. In this configuration, it may be inconvenient or difficult for some users to reach the system to adjust the oxygen flow. The remote control eliminates this inconvenience by enabling the user to adjust the oxygen flow using a handheld device. In one embodiment, the remote unit may be a custom controller designed to operate with the portable oxygen system. In another embodiment, the remote control may be a smart phone, tablet computer, or other portable computing device programmed to communicate with the portable oxygen delivery system. In this manner, user may control the portable oxygen delivery system with little greater effort that required to use a smart phone, further reducing the impact of the need for portable oxygen on the user's daily activities.

While certain embodiments have been described, it must be understood that various changes may be made and equivalents may be substituted without departing from the spirit or scope. In addition, many modifications may be made to adapt a particular situation or material to the teachings of the disclosure without departing from its spirit or scope.

What is claimed:

1. A container for storing oxygen under pressure comprising:
a chamber adapted to be worn partially around a user's waist and adapted for supplying oxygen to the user; the chamber defining a volume sized to contain at least 0.50 liquid liter of oxygen under pressure;
wherein the chamber is defined by a central portion extending between opposite side portions;
wherein each of the opposite side portions has a height greater than a maximum height of the central portion that further defines a void between the side portions and above the central portion, such that the chamber is generally U-shaped; and
wherein the chamber is further defined by an exterior surface of the chamber adjacent the user, and either
 a) the side portions are configured to wrap at least partially around the user's waist such that the exterior surface of the chamber adjacent the user is substantially concave, or
 b) the exterior surface of the chamber adjacent the user is substantially planar.

2. The container for storing oxygen under pressure of claim 1, wherein the volume is sized to contain at least 0.75 liquid liter of oxygen under pressure.

3. The container for storing oxygen under pressure of claim 1, wherein the void is sized to receive an oxygen delivery system.

4. The container for storing oxygen under pressure of claim 1, wherein the volume is sized to contain at least 750 liters gaseous equivalent capacity.

5. The container for storing oxygen under pressure of claim 1, wherein the chamber has a rigid exterior.

6. The container for storing oxygen under pressure of claim 1, wherein each of the opposite side portions has an interior side portion volume, and the central portion has an interior central portion volume, and the interior side portion volume is equal to or greater than the interior central portion volume.

7. The container for storing oxygen under pressure of claim 1, wherein the volume of the chamber is continuous without dividers or partitions within the volume.

8. The container for storing oxygen under pressure of claim 1, wherein the chamber has a lateral cross-section that is generally kidney shaped to conform to a user's torso.

9. The container for storing oxygen under pressure of claim 1, wherein the chamber has a lateral cross-section that is generally rectangular.

10. A portable oxygen delivery system comprising:
a chamber adapted to be worn partially around a user's waist, the chamber defining a volume sized to contain at least 0.50 liquid liter of oxygen under pressure, wherein the chamber is defined by a central portion extending between opposite side portions, wherein each of the opposite side portions has a height greater than a maximum height of the central portion that further defines a void between the side portions and above the central portion, such that the chamber is generally U-shaped,
an oxygen delivery system disposed in the void between the opposite side portions of the chamber, the oxygen delivery system including:
 an oxygen supply line coil connected to an output port of the chamber,
 a flow control valve configured to regulate a flow of gaseous oxygen to the user, and
 a lumen connector configured to receive a lumen for delivering the flow of gaseous oxygen to the user; and
wherein the chamber is further defined by an exterior surface of the chamber adjacent the user, and either a) the side portions are configured to wrap at least partially around the user's waist such that the exterior surface of the chamber adjacent the user is substantially concave, or b) the exterior surface of the chamber adjacent the user is substantially planar.

11. The portable oxygen delivery system of claim 10, wherein the volume is sized to contain at least 0.75 liquid liter of oxygen under pressure.

12. The portable oxygen delivery system of claim 10, wherein the portable oxygen delivery system is configured to provide a constant flow demand of at least 2 gaseous liters per minute for a duration of at least 5 hours.

13. The portable oxygen delivery system of claim 10, wherein the volume is sized to contain at least 750 liters gaseous equivalent capacity.

14. The portable oxygen delivery system of claim 10 further comprising a carrying case containing the chamber and oxygen delivery system, the carrying case configured to be secured around a user's waist.

15. The portable oxygen delivery system of claim 10, wherein the flow control valve is an electronically controlled flow control valve, and wherein the portable oxygen system further comprises a remote control configured to communicate wirelessly with the electronically controlled flow control valve to adjust the flow of gaseous oxygen to the user.

* * * * *